United States Patent [19]

Wong et al.

[11] Patent Number: 5,569,448

[45] Date of Patent: Oct. 29, 1996

[54] SULFATED NONIONIC BLOCK COPOLYMER SURFACTANTS AS STABILIZER COATINGS FOR NANOPARTICLE COMPOSITIONS

[75] Inventors: Sui-Ming Wong, Collegeville, Pa.; Ian M. Newington, Hazlemere, England; Elaine M. Liversidge; Gregory L. McIntire, both of West Chester, Pa.; Alan R. Pitt, Sandridge, United Kingdom; Jack M. Shaw, Aberdeen, Md.

[73] Assignee: Nano Systems L.L.C., Collegeville, Pa.

[21] Appl. No.: 378,022

[22] Filed: Jan. 24, 1995

[51] Int. Cl.$^6$ .................................................. A61K 9/14
[52] U.S. Cl. ..................... 424/9.45; 424/489; 424/490; 424/213.36
[58] Field of Search ............................... 424/489, 490, 424/9.45; 427/213.36

[56] References Cited

U.S. PATENT DOCUMENTS

| | | | |
|---|---|---|---|
| 4,304,691 | 12/1981 | Farmer, III et al. | 252/545 |
| 5,145,684 | 9/1992 | Liversidge et al. | 424/489 |
| 5,318,767 | 6/1994 | Liversidge et al. | 424/4 |
| 5,340,564 | 8/1994 | Illig et al. . | |

Primary Examiner—Jeffrey C. Mullis
Attorney, Agent, or Firm—Rudman & Balogh

[57] ABSTRACT

This invention provides a composition comprised of nanoparticles containing a therapeutic or diagnostic agent having a block copolymer linked to at least one anionic group as a surface modifier adsorbed on the surface thereof and a method of making such nanoparticles. The compositions exhibit unexpectedly improved autoclave stability, reduced macrophage uptake, improved toxicological profiles and facilitate particle size reduction such that milling time can be reduced and/or sterile filtration of the nanoparticles can be accomplished.

5 Claims, No Drawings

SULFATED NONIONIC BLOCK COPOLYMER SURFACTANTS AS STABILIZER COATINGS FOR NANOPARTICLE COMPOSITIONS

FIELD OF THE INVENTION

This invention relates to therapeutic and diagnostic compositions containing a surfactant and to a method for the preparation thereof.

BACKGROUND OF THE INVENTION

U.S. Pat. No. 5,145,684 discloses particles of a drug substance having a surface modifier absorbed on the surface thereof and methods for the preparation thereof by wet grinding. These particles have demonstrated significant pharmaceutical utility. Suitable surface modifiers described include various polymers. The surface modifiers disclosed include Pluronic F68 and F108, which are block copolymers of ethylene oxide and propylene oxide; Tetronic 908, which is a tetrafunctional block copolymer derived from sequential addition of propylene oxide and ethylene oxide to ethylene diamine; sodium dodecylsulfate, dialkyl esters of sodium sulfosuccinic acid such as Aerosol OT™, sodium lauryl sulfate, and Triton™ X-200.

U.S. Pat. No. 5,318,767 discloses X-ray contrast compositions comprising particles of an X-ray contrast agent having a surface modifier absorbed on the surface thereof and methods for the preparation thereof by wet grinding. The above-noted surface modifiers are also disclosed as being useful therein. These X-ray contrast compositions have demonstrated remarkable utility in X-ray medical dianostic imaging procedures.

U.S. Pat. No. 5,340,564 discloses therapeutic and diagnostic compositions with Olin-10 G, i.e., p-isononylphenoxypoly(glyciodol) having improved autoclave stability.

However, sterilization of therapeutic and diagnostic agents in nanoparticulate form stabilized by a surface modifier is difficult. Filtration using a filter of 0.22 μm mesh size is sufficient to remove most bacteria, but the nanoparticles, due to their sizes, cannot be sterile filtered without accounting for substantial drug losses. Conventional autoclaving (steam heat) at 121° C. generally results in substantial increase in particle size, rendering the resulting particles unusable. One possible explanation is that the aggregation of nanoparticles upon heating is related to the phase separation of the surface modifier (surfactant) at or below the sterilization temperature where the bound surfactant molecules are likely to dissociate from the nanoparticles and precipitate, leaving the nanoparticles unprotected. The unprotected nanoparticles can then aggregate into clusters of particles. Upon cooling, the surfactant redissolves into the solution, which then coats the aggregated particles and prevents them from dissociating into smaller ones.

Additional difficulties of some of the above-described surfactants relate to biological usage and wet grinding method.

For example, some of the above-described surfactants have demonstrated less than Superior toxicological profiles such as T908, DOSS, Pluronic S127 and Olin 10G. In addition, these prior art surfactant coatings, when adsorbed to nanoparticles, on some occasions, have exhibited less than desirable uptake of nanoparticles by macrophages.

Moreover, the wet grinding methods described in the patents noted above often entail grinding for days or even weeks which can be undesirable, e.g., from the standpoint of process scale-up.

Consequently, it would be highly desirable to provide surfactant coatings for nanoparticles which provide improved resistance to particle size increase during autoclaving, exhibit improved toxicological profiles, minimize macrophage uptake and facilitate particle size reduction such that milling time can be reduced and/or sterile filtration of the nanoparticles can be accomplished without substantial particle losses.

SUMMARY OF THE INVENTION

We have discovered surfactant coatings for nanoparticles which provide unexpected resistance to nanoparticle size growth during autoclaving, inhibit macrophage uptake, has an improved safety profile, and facilitate particle size reduction.

More specifically, in accordance with this invention, there is provided a composition comprised of nanoparticles containing a therapeutic or diagnostic agent having a block copolymer linked to at least one anionic group as a surface modifier absorbed on the surface thereof.

It is an advantageous feature of this invention that surfactants are provided for nanoparticle compositions which allow autoclaving of the nanoparticles without the concomitant growth in particle size and which exhibit an improved toxicological profile.

It is another advantageous feature of this invention that nanoparticle compositions are provided which minimize macrophage uptake.

Yet another advantageous feature of this invention is that nanoparticle compositions are provided in a narrow particle size distribution.

Still another advantageous feature of this invention is that a surfactant coating is provided for nanoparticles which facilitates particle size reduction, thus reducing milling time and potentially enabling sterile filtration of the nanoparticles to be accomplished without substantial particle losses.

These and other advantages will become readily apparent upon reference to the following description of preferred embodiments.

DESCRIPTION OF PREFERRED EMBODIMENTS

This invention is described hereinafter primarily in connection with nanoparticles containing a therapeutic or diagnostic agent having a block copolymer linked to at least one anionic group as a surface modifier adsorbed on the surface thereof.

Surface modifiers useful herein are block copolymers linked to at least one anionic group. The polymers contain at least one, and preferably two, three, four or more anionic groups per molecule. Preferred anionic groups include sulfate, sulfonate, phosphonate, phosphate and carboxylate groups. The anionic groups are covalently attached to the nonionic block copolymer. The nonionic sulfated polymeric surfactant has a molecular weight of 1,000–50,000, preferably 2,000–40,000 and more preferably 3,000–30,000. In preferred embodiments, the polymer comprises at least about 50%, and more preferably, at least about 60% by weight of hydrophilic units, e.g., alkylene oxide units. The reason for this is that the presence of a major weight proportion of hydrophilic units confers aqueous solubility to the polymer. The block copolymers useful herein are known compounds and/or can be readily prepared by techniques well known in the art.

A preferred class of block copolymers useful in preparing surface modifiers for use herein includes sulfated block copolymers of ethylene oxide and propylene oxide. These block copolymers, in an unsulfated form, are generically called poloxamers and are commercially available as Pluronics™. Specific examples of the unsulfated block copolymers include F68, F108, and F127.

Another preferred class of block copolymers useful herein include tetrafunctional block copolymers derived from sequential addition of propylene oxide and ethylene oxide to ethylene diamine. These polymers, in an unsulfated form, are commercially available as Tetronics™.

Another preferred class of block copolymers contain at least one polyethylene oxide (PEO) block as the hydrophilic portion of the molecule and at least one polybutylene oxide (PBO) block as the hydrophobic portion. Particularly preferred copolymers of this class are diblock, triblock, and higher block copolymers of ethylene oxide and butylene oxide, such as are represented, for example, by the following structural formula:

Highly preferred surface modifiers include triblock copolymers of the structure 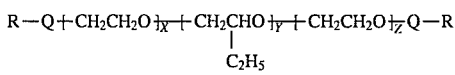 having molecular weights of 3800 and 5000 which are commercially available from Dow Chemical, Midland, Mich., and are hereinafter referred to as B20-3800 and B20-5000. These surface modifiers contain about 80% by weight PEO. In a preferred embodiment, the surface modifier is a triblock polymer linked to an anionic group having the structure:

$$R-Q+CH_2CH_2O\}_{\overline{X}}+CH_2CHO\}_{\overline{Y}}+CH_2CH_2O\}_{\overline{Z}}Q-R$$
$$|$$
$$C_2H_5$$

wherein Q is an anionic group, R is H or a metal cation such as $Na^+$, $K^+$ and the like, X is 15–700, Y is 5–200 and Z is 15–700.

While the applicants do not wish to be bound by theoretical mechanisms, it is believed that the presence of the anionic group increases the ionic character and polarity of the surface modifier and provides both electrostatic and steric stabilization, thus reducing the tendency of the surface modifier to phase separate during steam heat autoclaving.

The surface modifier useful herein can be prepared by techniques known in the art. Thus, the anionic group can be linked to the block copolymer using conventional linking technology. For example, the sulfated nonionic block copolymers useful herein can be prepared from the unsulfated form of the polymers by conventional sulfation techniques. For example, sulfated F68, F108, F127 . . . can be prepared by dissolving the unsulfated nonionic block copolymer in a suitable solvent, e.g., 1,2-dichloroethane and contacting the dissolved polymer with a source of sulfate ions, e.g., chlorosulphonic acid. Suitable solvents include tetrahydroform, dichloromethane, chloroform, dioxane and 1,2-dimethoxyethane. Suitable sources of sulfate ions include sulfur trioxide and sulfur trioxide-pyridine complex. Sulfation can take place at temperatures from about 25° C. to 50° C. and higher. Contact times can range from seconds to several hours. The reaction can take place at atmospheric pressure. However, higher and lower reaction pressures are contemplated. In a similar manner, block copolymers can be reacted with a source of sulfonate, phosphate or phosphonate ions to form the surface modifiers useful herein. In the case of carboxylate anions, direct oxidation or the addition of a carboxyl-containing compound such as a bromoacetate is employed.

The nanoparticles useful in the practice of this invention can be prepared according to the methods disclosed in U.S. Pat. No. 5,145,684 and U.S. Pat. No. 5,318,767.

Briefly, a method for the preparation of a nanoparticle composition according to this invention includes the steps of introducing a diagnostic or therapeutic agent, a liquid medium, grinding media, and optionally, a surface modifier into a grinding vessel; wet grinding to reduce the particle size of the agent to less than about 1000 nm; and separating the particles and the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions.

A general procedure for preparing the particles useful in the practice of this invention follows. The therapeutic of diagnostic agent selected is obtained commercially and/or prepared by techniques known in the art, in a conventional coarse form. It is preferred, but not essential, that the particle size of the coarse therapeutic of diagnostic substance selected be less than about 100 μm as determined by sieve analysis. If the coarse particle size of that agent is greater than about 100 μm, then it is preferred that the coarse particles of the therapeutic or diagnostic agent be reduced in size to less than 100 μm using a conventional milling method such as airier or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (2/2). It is preferred, but not essential, that the surface modifier be present in the premix. The concentration of the surface modifier can vary from about 0.1 to 90%, and preferably is 1–75%, more preferably 2–50% and most preferably 5–45% by weight based on the total combined weight of the drug substance and surface modifier. The apparent viscosity of the premix suspension is preferably less than about 1000 centipoise.

The premix can be used directly by wet grinding to reduce the average particle size in the dispersion to less than about 1000 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogenous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, a planetary mill and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, media with higher density, e.g., glass (2.6 g/cm$^3$), zirconium silicate (3.7 g/cm$^3$), and zirconium oxide (5.4 g/cm$^3$), are generally preferred for more efficient milling. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful. In addition, polymeric media having a density typically from 1 to 2 g/cm$^3$ are also expected to be useful under certain milling conditions. The grinding media can be a polymeric media such as described in European Patent Application No. 600,528.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperature of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 2–50%, and most preferably 5–45% by weight based on the total weight of the dry particle. The surface modifier preferably is present in an amount exceeding the critical miscelle concentration.

Therapeutic and diagnostic agents useful in the composition of the present invention include those disclosed in U.S. Pat. No. 5,145,684, and U.S. Pat. No. 5,318,767 whose disclosures are incorporated herein by reference. Preferred diagnostic agents include the X-ray imaging agent ethyl 3,5-diacetamido-2,4,6 -triiodobenzoate; 6-ethoxy-6-oxohexyl-3,5 -bis(acetamido)-2,4,6-triiodobenzoate; ethyl-2-(3,5 -bis(acetamido)-2,4,6-triiodobenzoyloxy)butyrate; ethyl diatrizoxyacetate; ethyl 2-(3,5-bis(acetamido)-2,4,6 -triiodobenzoyloxy)propionate; N-ethyl 2-(3,5 -bis(acetamido)-2,4,6-triiodobenzoyloxy) acetamide; isopropyl 2-(3, 5-bis(acetamido)-2,4,6 -triiodobenzoyloxy) acetamide; diethyl 2-(3,5 -bis(acetamido)-2,4,6-triiodobenzoyloxy) malonate; and ethyl 2-(3,5-bis(acetamido)-2,4,6-triiodobenzoyloxy) phenylacetate. Suitable diagnostic agents are also disclosed in U.S. Pat. No. 5,260,478; U.S. Pat. No. 5,264,610; U.S. Pat. No. 5,322,679 and U.S. Pat. No. 5,300,739.

A method for preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 1000 nm; and separating the particles and the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method can be carried out under aseptic conditions. Thereafter, the nanoparticle composition preferably is subjected to a sterilization process.

As noted elsewhere herein, sterile filtration will not provide adequate sterilization for nanoparticles without causing significant loss of active material. Although the compositions of this invention can be sterile filtered, other methods of sterilization can also be employed. For example, steam or moist heat sterilization at temperatures of about 121° C. for a time period of about 20 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

It is an advantageous feature of this invention that nanoparticle compositions are provided having unexpectedly improved autoclave stability in the substantial absence of secondary stability enhancing agents. Nonetheless, the therapeutic or diagnostic agent in the form of surface modified nanoparticles can be associated with a cloud point modifier to further enhance stability during steam heat autoclaving, i.e., the cloud point modifier can further reduce particle aggregation during heat sterilization. Preferred cloud point modifiers include nonionic cloud point modifiers, such as those described in U.S. Pat. No. 5,346,702 including polyethylene glycols such as PEG 400, propylene glycol, ethanol, hydroxypropylcyclodextrin and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as those described in U.S. Pat. No. 5,336,507 including diacylphosphatidyl glycerol and dimyristoylphosphatidyl glycerol. The cloud point modifier can be present in an amount of 0.005–50%, preferably 0.01–30% and more preferably 0.05–20% by weight based on the total weight of the nanoparticle composition.

Therapeutic and diagnostic compositions according to this invention include the particles described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step administering to the mammal in need of treatment an effective amount of the above-described therapeutic composition. The selected dosage level of the therapeutic substance for treatment is effective to obtain a desired therapeutic response for a particular composition and method of administration. The selected dosage level therefore, depends upon the particular drug substance, the desired therapeutic effect, on the route of administration, on the desired duration of treatment and other factors.

In a preferred embodiment, the diagnostic compound is an X-ray contrast agent, such as an iodinated X-ray contrast agent. Thus, the diagnostic compositions of this invention include an X-ray contrast composition comprising particles containing an X-ray contrast agent and a physiologically acceptable carrier therefor. For example, the particles can be dispersed in an aqueous liquid which serves as the carrier for the X-ray contrast agent. Other suitable carriers include liquid carriers such as mixed aqueous and nonaqueous solvents, such as alcohol; gels; gases; such as air; and powders.

The X-ray contrast compositions can comprise from about 1–99.9, preferably 2–45 and more preferably 10–30% by weight of the above-described particles, the remainder of the composition being the carrier, additives and the like. Compositions up to about 100% by weight of the particles are contemplated when the composition is in a lyophilized form.

The X-ray contrast composition can contain one or more conventional additives used to control and/or enhance the properties of the X-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject the above-described X-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to X-rays to produce an X-ray image pattern. The image pattern can then be visualized. For example, any X-ray visualization technique, preferably, a high contrast technique such as computed tomography, can be applied in a convention manner. Alternatively, the image pattern can be observed directly on an X-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like. In addition to preferred applications, i.e., for blood pool, liver, spleen and lymph node imaging, the X-ray contrast compositions of this invention are also expected to be useful as an angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mg I/kg, can be effective.

The X-ray contrast composition can contain one or more conventional additives used to control and/or enhance the properties of the X-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

This invention further relates to a method of making nanoparticles containing a diagnostic or therapeutic agent having a block copolymer linked to at least one anionic group as a surface modifier adsorbed on the surface thereof, comprises of contacting the diagnostic or therapeutic agent with the sulfated nonionic block copolymer for a time and under conditions sufficient to form a stabilized nanoparticle. Contacting can be by admixing a suspension of the diagnostic or therapeutic agent with a solution of the block copolymer such as described above.

The following examples further illustrate the invention.

EXAMPLE 1. PREPARATION OF SULFATED T908

T908 (25 g) was dissolved in 1,2-dichloroethane (500 ml) and chlorosulphonic acid (0.43 ml, 6 molar equivalents) was added. After 10 min of vigorous stirring, the solution was heated to 50° C. and this temperature was maintained for 2.5 hours. On cooling the solvent was evaporated and the residue dissolved or dispersed in water (400 ml) and the pH adjusted to a value of approximately 10 by addition of dilute aqueous sodium hydroxide. The water was removed by heating on a steam bath (or freeze-drying). The residue was dissolved in methanol and the insoluble inorganic salts were filtered off. The methanol was removed by distillation under reduced pressure, and the T908 tetrasulphate dried in a vacuum oven (T,<40° C.). Elemental microanalysis verified that the sulfur content was consistent with 4 sulfate groups per molecule.

EXAMPLE 2. PREPARATION OF SULFATED F108

Pluronic F108 (35 g) was dissolved in 1,2 dicholorethane (200 ml). Cholosulfonic acid (0.7 ml, 4 molar equivalent)

was added and the mixture heated at 45°–50° C. for 3 hr. On cooling, the solvent was removed by evaporation at reduced pressure. The residue was dissolved in warm water (40°–50° C., 200 ml or minimum possible) and adjusted to ~pH 10 with sodium hydroxide solution. Ethanol (>1000 ml) was added and the solution evaporated under reduced pressure. Further additions of ethanol with evaporation gave a white solid which was dried at 40° C. in the vacuum. Elemental microanalysis verified that the sulfur content was consistent with 2 sulfate groups per molecule.

EXAMPLE 3. PREPARATION OF SULFATED B20-3800

Polybutylene oxide, polyethylene oxide copolymer B20-3800 (8.8 g) was dissolved in 1,2 dichloroethane (200 ml). The solution was purged with nitrogen gas for 20 mins. followed by the addition of chlorosulfonic acid (0.7 ml, 4 molar equivalent). The mixture was heated at 45°–50° C. for 3 hours under nitrogen atmosphere. On cooling, the solvent was removed by evaporation at reduced pressure. The residue was dissolved in warm water and adjusted to ~pH 10 with sodium hydroxide followed by work up procedures as used in example 2 to afford B20-3800 disulfate. Elemental microanalysis verified that the sulfur content was consistent with 2 sulfate groups per molecule.

EXAMPLE 4. PREPARATION OF SULFATED B20-5000

The method described in Example 4 was repeated except that polybutylene oxide, polyethylene oxide copolymer B20-5000 (11.6 g) was used in place of the copolymer B20-3800. Elemental analysis verified the presence of 2 sulfate groups per molecule.

EXAMPLES 5–12. PREPARATION OF NANOCRYSTAL FORMULATION AND AUTOCLAVE STABILITY EVALUATION

The following formulations were prepared at 15% diagnostic agent and 4% surfactant (w/v). A 6% stock solution was prepared by dissolving 600 mg of T908-tetrasulfate, F108-disulfate, B20-3800-disulfate or B20-5000-disulfate surfactants in 10 ml deionized water. To each 15 ml amber colored bottle, 7.5 ml $ZrSiO_4$ beads of size 1.1 mm, 562 mg of compound A (ethyl 3,5-diacetamido-2,4,6-triiodobenzoate) or compound B (6-ethoxy-6-oxohexyl-3,5-bis(acetamido)- 2,4,6-triiodobenzoate), 2.5 ml of 6% stock surfactant solution and 0.994 ml deionized water were added. The sample bottle was sealed and placed on a roller mill running at 160 rpm for 5 days. At day 5, aliquot of samples were diluted 50 fold with deionized water for particle size measurement by Photon Correlation spectroscopy (Microtrac).

For terminal sterilization, 1 ml of nanocrystal formulations prepared above was pipetted into a 2 ml serum vial. After sealing with rubber septum and aluminum cap, the samples were subjected to autoclave at 121° C. for 20 min. On cooling to room temperature, aliquot of samples were retreated from the vial and diluted 50 fold with deionized water for particle size measurement by Photon Correlation spectroscopy (Microtrac).

| | | | Mean Particle size (nm) | |
|---|---|---|---|---|
| Example | Core | Surfactant | Before Auto. | After Auto. |
| 5 | Compound A | T908-tetrasulfate | 154 | 233 |
| 6 | Compound A | F108-disulfate | 159 | 245 |
| 7 | Compound A | B20-5000-disulfate | 107 | 180 |
| 8 | Compound A | B20-3800-disulfate | 118 | 211 |
| A | Compound A | F108 | 130 | >500 |
| B | Compound A | T8-908 | 241 | >500 |
| C | Compound A | B20-5000 | 106 | >500 |
| D | Compound A | B20-3800 | 110 | >500 |
| 9 | Compound B | T908-tetrasulfate | 146 | 256 |
| 10 | Compound B | F108-disulfate | 145 | 233 |
| 11 | Compound B | B20-5000-disulfate | 110 | 199 |
| 12 | Compound B | B20-3800-disulfate | 110 | 213 |
| E | Compound B | F108 | 130 | >500 |
| F | Compound B | T8-908 | 144 | >500 |
| G | Compound B | B20-5000 | 102 | >500 |
| H | Compound B | B20-3800 | 94 | >500 |

Compared to the corresponding commercially available copolymeric surfactants under identical milling and autoclave conditions, this data demonstrates that the sulfated block copolymers alone resulted in unexpectedly limited increases in particle size during terminal sterilization of nanocrystal formulations.

In addition, tail vein injection of a 4% solution of T908-disulfate, F108-disulfate and B20 -5000-disulfate at 30 ml/Kg was well tolerated by mice.

T908-tetrasulfate, F108-disulfate, B20-5000 -disulfate also significantly inhibited the uptake of polystyrene particle by macrophages while B20-3800 -disulfate had less effect. The degree of minimal macrophage uptake was found to be as follows: F108 -disulfate>T908-tetrasulfate B20-5000-disulfate>B20 -3800-disulfate.

The invention has been described in detail with particular reference to certain preferred embodiments thereof, but it will be understood that variations and modifications can be effected within the spirit and scope of the invention.

We claim:

1. A composition comprised of nanoparticles containing a therapeutic or diagnostic agent having a surface modifier adsorbed on the surface thereof, wherein said composition is autoclavable and after autoclaving the nanoparticles have an average particle size of less than 500 nm, and wherein the surface modifier is a triblock copolymer having the structure

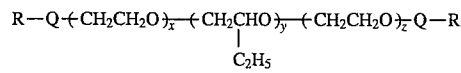

wherein Q is a sulfate group,
R is H or a metal ion,
x is 15–700,
y is 5–200, and
z is 15–700.

2. The composition of claim 1 wherein said copolymer comprises at least 50% by weight of ethylene oxide units.

3. The composition of claim 1 wherein said diagnostic agent is ethyl 3,5-diacetoamido-2,4,6-triiodobenzoate.

4. The composition of claim 1 wherein said diagnostic agent is 6-ethoxy-6-oxohexyl-3,5-bis(acetamido)-2,4,6 -triiodobenzoate.

5. A method of making nanoparticles containing a diagnostic or therapeutic agent having a surface modifier adsorbed on the surface thereof comprised of contacting said diagnostic or therapeutic agent with said surface modifier for a time and under conditions sufficient to form a stabilized nanoparticle, wherein, said resultant nanoparticles are autoclavable and after autoclaving the nanoparticles have an average particle size of less than 500 nm, and wherein the surface modifier is with a triblock copolymer having the structure $$R-Q\!-\!(CH_2CH_2O)_x\!-\!(CH_2CHO)_y\!-\!(CH_2CH_2O)_z\!-\!Q-R$$
$$|$$
$$C_2H_5$$

wherein Q is a sulfate group,
R is H or a metal ion,
x is 15–700,
y is 5–200, and
z is 15–700.

* * * * *